United States Patent
Bonnin et al.

(10) Patent No.: US 10,022,044 B2
(45) Date of Patent: Jul. 17, 2018

(54) METHOD OF VISUAL TESTING OF AN INDIVIDUAL AND ASSOCIATED DEVICE

(71) Applicant: ESSILOR INTERNATIONAL (COMPAGNIE GENERALE D'OPTIQUE), Charenton-le-Pont (FR)

(72) Inventors: Thierry Bonnin, Charenton-le-Pont (FR); Ahmed Haddadi, Charenton-le-Pont (FR); Sarah Marie, Charenton-le-Pont (FR)

(73) Assignee: ESSILOR INTERNATIONAL (COMPAGNIE GENERALE D'OPTIQUE, Charenton-le-Pont (FR)

( * ) Notice: Subject to any disclaimer, the term of this patent is extended or adjusted under 35 U.S.C. 154(b) by 0 days.

(21) Appl. No.: 15/312,757

(22) PCT Filed: May 19, 2015

(86) PCT No.: PCT/FR2015/051313
§ 371 (c)(1),
(2) Date: Nov. 21, 2016

(87) PCT Pub. No.: WO2015/177458
PCT Pub. Date: Nov. 26, 2015

(65) Prior Publication Data
US 2017/0181617 A1    Jun. 29, 2017

(30) Foreign Application Priority Data
May 20, 2014    (FR) ...................................... 14 54545

(51) Int. Cl.
*A61B 3/10*    (2006.01)
*A61B 3/00*    (2006.01)
(Continued)

(52) U.S. Cl.
CPC .............. *A61B 3/032* (2013.01); *A61B 3/024* (2013.01); *G02C 13/005* (2013.01)

(58) Field of Classification Search
CPC .... G02C 13/005; G02C 13/003; G02C 7/027; A61B 3/111; A61B 3/0025
(Continued)

(56) References Cited

U.S. PATENT DOCUMENTS

| 5,270,750 A | 12/1993 | Aulhorn et al. |
| 2010/0195045 A1 | 8/2010 | Nauche et al. |
| 2012/0033178 A1* | 2/2012 | Chauveau ............ G02C 13/005 351/204 |

FOREIGN PATENT DOCUMENTS

| CN | 1438852 A | 8/2003 |
| CN | 101356468 A | 1/2009 |

(Continued)

OTHER PUBLICATIONS

International Search Reported, dated Sep. 2, 2015, from corresponding PCT Application.

*Primary Examiner* — Mohammed Hasan
(74) *Attorney, Agent, or Firm* — Young & Thompson (57) ABSTRACT

A method of visual testing of an individual (10) includes the steps of: a) placing the individual at a predetermined observation distance (D1) from a display surface (21) at which the individual observes, with a natural head carriage, the display surface; b) displaying, on the display surface, a visual test including at least one test image (22) in a visual field of the individual; and c) determining, on the display surface, a boundary (23) of zones of optimal/degraded vision of the test image by the individual in the configuration resulting from steps a) and b), the boundary delimiting respectively a zone of optimal vision (23A) and a zone of degraded vision (23B) of the visual field, for which zones the individual (Continued)

indicates that he sees the test image of the visual test in an optimal manner, respectively in a degraded manner.

14 Claims, 3 Drawing Sheets

(51) Int. Cl.
  *A61B 3/032* (2006.01)
  *A61B 3/024* (2006.01)
  *G02C 13/00* (2006.01)
(58) Field of Classification Search
  USPC .................................................. 351/200–246
  See application file for complete search history.

(56) References Cited

FOREIGN PATENT DOCUMENTS

| | | |
|---|---|---|
| CN | 103429140 A | 12/2013 |
| EP | 1 442 695 A2 | 8/2004 |
| EP | 2 137 569 A1 | 12/2009 |
| GB | 2 267 159 A | 11/1993 |
| WO | 96/34555 A1 | 11/1996 |
| WO | 2008/129168 A1 | 10/2008 |

* cited by examiner

METHOD OF VISUAL TESTING OF AN INDIVIDUAL AND ASSOCIATED DEVICE

TECHNICAL FIELD OF THE INVENTION

The present invention generally relates to the field of ophthalmic optics.

It more particularly relates to a method and device for testing the vision of an individual, allowing the vision quality of this individual to be objectively demonstrated.

PRIOR ART

During a visit to an opticians, an individual desiring to evaluate the quality of his vision, with or without a piece of vision-correcting ophthalmic equipment, is generally tested with a vision-testing method that may be considered to be subjective in the sense that the vision quality of the individual is not observed directly and no concrete measurement result can be presented to the individual.

Furthermore, the results of the vision-testing methods conventionally employed give no indication to the optician as regards the accessible zones of the visual field that the individual sees clearly on the one hand and hazily on the other.

SUBJECT OF THE INVENTION

In order to remedy the aforementioned drawbacks of the prior art, the present invention provides a vision-testing method allowing an objective demonstration of the vision quality of the individual and the bounds of said quality in the visual field of the individual to be determined.

More particularly, according to the invention a method for testing the vision of an individual wearing a piece of vision-correcting ophthalmic equipment is provided, said method including the following steps:

a) placing said individual at a predetermined observation distance from a displaying area, at which said individual observes, with a natural cephalic carriage, said displaying area, b) displaying, on said displaying area, a visual test comprising at least one test image, and c) determining, in said displaying area, a border of zones of optimal/degraded vision of said test image by the individual in the configuration resulting from steps a) and b), said border respectively bounding, in a visual field of said individual equipped with said piece of ophthalmic equipment, a zone of optimal vision and a zone of degraded vision of said visual field, for which zones said individual indicates whether he respectively sees optimally or degradedly said test image of the visual test through said piece of vision-correcting ophthalmic equipment.

The first step is a step of positioning the individual, which allows said individual to be placed under observation conditions similar to those that he would adopt in everyday life.

The predetermined observation distance selects the type of vision that it is desired to measure with the vision-testing method: near vision, far vision, or intermediate vision.

The second step is a displaying step comprising presenting to the individual a test image, generally formed of a text intended to be read by said individual, who is placed at the observation distance determined beforehand in the first step.

By virtue of the vision-testing method according to the invention, it is possible to obtain information relating to the vision quality of the individual inside his visual field.

This vision quality is noteworthy in that, on the one hand, a zone of optimal vision and, on the other hand, a zone of degraded vision are determined, these two zones being bounded by the border of zones of optimal/degraded vision.

In the zone of optimal vision, the individual declares that he can clearly see said test image of the visual test, whereas in the zone of degraded vision the individual declares that said test image is hazy.

It is left up to the individual to choose the criterion to use to categorize the zone of optimal vision and the zone of degraded vision.

The border of zones of optimal/degraded vision thus embodies the vision quality of said individual.

One particularly advantageous application of the invention is in the evaluation of the near-vision vision quality of an individual wearing a piece of vision-correcting ophthalmic equipment comprising one or two progressive lenses.

The following are other nonlimiting and advantageous features of the vision-testing method according to the invention:

the vision-testing method includes a step d), subsequent to step c), that consists in recording a border indicator representative of said border of zones of optimal/degraded vision;

said border indicator corresponds to the position and/or the shape of said border;

the vision-testing method includes a step e), subsequent to step d), that consists in comparing said border indicator with a reference indicator, an in deducing from the preceding comparison an optical performance of the individual under the observation conditions of steps a) and b);

steps a) to d) being executed at least a first time, with an individual equipped with a first piece of vision-correcting ophthalmic equipment, to determine a first border and to record a first border indicator, and the individual actually or virtually being equipped with a second piece of vision-correcting ophthalmic equipment that is different from said first piece of ophthalmic equipment:

a second border of zones of optimal/degraded vision of said test image by said individual is determined in said displaying area in the configuration resulting from steps a) and b), said second border respectively bounding a second zone of optimal vision and a second zone of degraded vision of said visual field, for which zones said individual actually or virtually equipped with said second piece of ophthalmic equipment indicates or is assumed to respectively see optimally or degradedly said test image of the visual test, a second border indicator representative of said second border of zones of optimal/degraded vision is recorded, said first border indicator and said second border indicator are compared, and from the preceding comparison an optical performance of the individual under the observation conditions of steps a) and b) is deduced;

said second border is determined by executing a second time steps a) to c) for said individual equipped with a real example of said second piece of ophthalmic equipment;

said second border is determined by numerical simulation of the visual field of said individual virtually equipped with said second piece of ophthalmic equipment and observing the test image under the same conditions as those of steps a) and b);

said vision-testing method includes a step f) in which, on a useful area of the displaying area corresponding to the zone of optimal vision of the visual field of the individual equipped with said piece of vision-correcting ophthalmic equipment, a complementary visual test comprising at least one complementary test image is displayed;

the test image, the first border and the second border are displayed in superposition;

in step c), said border is determined for a given position of the head of the individual with respect to the displaying area;

in step b), the position of the test image of said visual test in said displaying area depends on the position of the head of the individual with respect to the displaying area;

in step c), said border of zones of optimal/degraded vision is determined by the individual who draws said border in said displaying area.

The invention also provides a device for testing the vision of an individual wearing a piece of vision-correcting ophthalmic equipment, said device including:

displaying means suitable for displaying on a displaying area, a visual test comprising at least one test image in a visual field of an individual;

means for inputting, in said displaying area, a border of zones of optimal/degraded vision of said test image by the individual, said border respectively bounding a zone of optimal vision and a zone of degraded vision of said visual field, for which zones said individual indicates whether he respectively sees optimally or degradedly said test image of the visual test through said piece of vision-correcting ophthalmic equipment;

means for storing in memory the position and shape of said border in the displaying area; and means for pinpointing the posture of the head of said individual with respect to the display means.

Advantageously, the vision-testing device according to the invention includes drawing means suitable for superposing said test image and at least said border.

DETAILED DESCRIPTION OF AN EXEMPLARY EMBODIMENT

The description which follows with reference to the appended drawings, which are given by way of nonlimiting examples, will make it easy to understand the essence of the invention and how it can be achieved.

Figure 1:
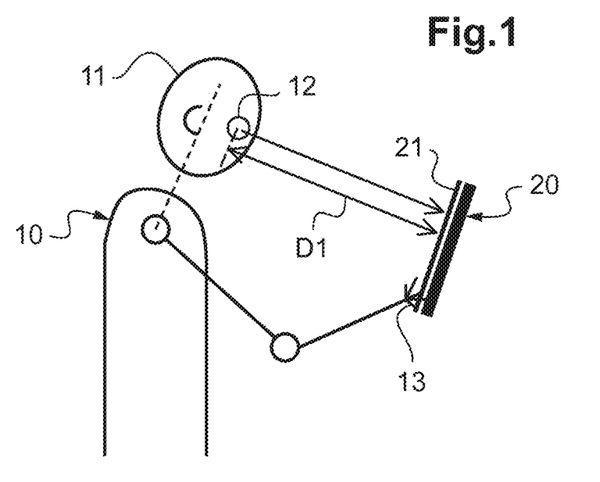
FIG. 1 is a schematic profile view of an individual without a piece of ophthalmic equipment observing, in their near vision and with a natural cephalic carriage, a text displayed on a digital touch tablet.
Figure 3:
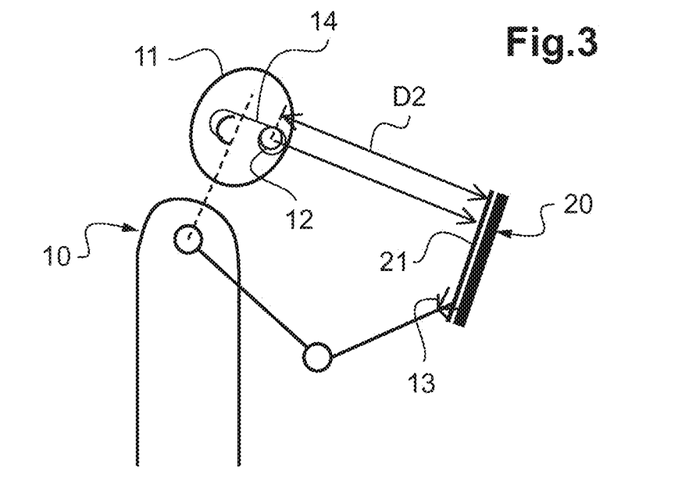
FIG. 3 is a schematic profile view of the individual in FIG. 1, equipped with progressive lenses and observing, in their vision through said progressive lenses and with a natural cephalic carriage, the text displayed on the digital touch tablet in FIG. 2.

FIGS. 1 and 3 show an individual 10 holding between his hands a vision-testing device 20 by virtue of which vision-testing methods according to the invention may be implemented in order to test the vision of this individual 10.

Firstly, the constituent means of this vision-testing device 20 will be described and, secondly, various exemplary vision-testing methods implementable by virtue of this device 20 will be described.

In FIGS. 1 and 3 only the head 11, the eyes 12 and the hands 15 of the tested individual 10 have been shown. Only the right eye 12 of the individual 10 may be seen in FIGS. 1 and 3.

The vision-testing device 20 firstly includes displaying means. In the illustrated example, these displaying means consist of a touch tablet.

As a variant, the display means may comprise a monitor, or a projector associated with a screen onto which an image or text is projected, or quite simply of a more conventional medium such as a sheet of paper.

The tablet 20 is designed and programmed to display a visual test in a displaying area, here a digital and preferably color screen 21.

In the various embodiments of the invention, the visual test displayed on the screen 21 of the tablet 20 comprises at least one test image 22 (see FIGS. 2 and 6 for example), this test image 22 preferably being easily recognizable or understandable by an average individual.

The test image 22 is preferably a conventional image, i.e. an image encountered in everyday life, or a text formed from easily intelligible words and phrases.

Figure 2:
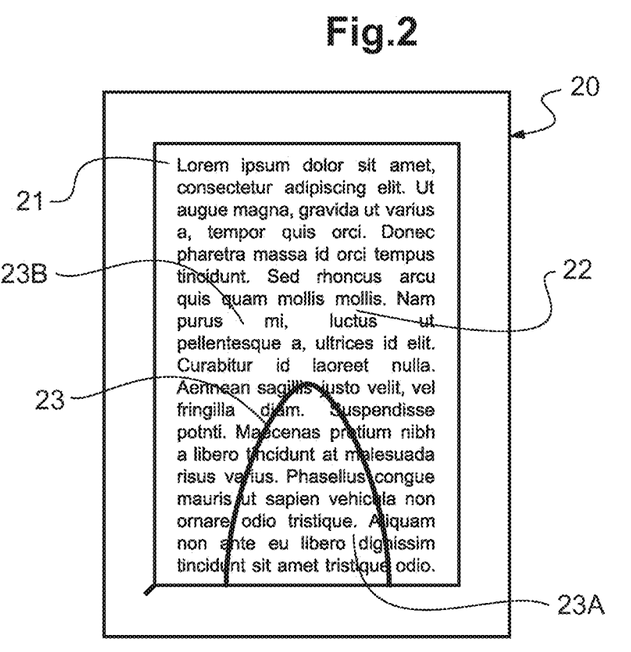
FIG. 2 is a schematic front view of the touch tablet in FIG. 1, on which is displayed in superposition a zone border determined by the individual.

The test image 22 here comprises a text, a journal article for example (see for example FIG. 2).

As a variant, the test image may comprise letters, words, numerals, numbers, simple images or patterns, for example optionally repetitive geometric patterns that are possibly regularly arranged with respect to one another.

The screen 21 of the tablet 20 is, under test conditions, turned toward the individual 10 so that the latter can see the visual test displayed on the screen 21 (see FIGS. 1 and 3).

As FIGS. 1 and 3 show, the individual 10 observes the screen 21 of the tablet 20 at a certain observation distance, referenced D1 in FIG. 1 and D2 in FIG. 3.

This observation distance D1, D2 is predetermined depending on the nature of the visual test that it is desired for the individual 10 to carry out.

Specifically, depending on whether it is desired to test near vision, far vision, or vision intermediate between near and far vision, a suitable observation-distance range is selected.

More precisely, to perform a visual test intended to evaluate the vision quality of an individual:

in near vision: an observation distance smaller than about 40 centimeters is chosen, in far vision: an observation distance larger than about 4 meters is chosen, and in intermediate vision: an observation distance comprised between 40 cm and 4 m is chosen.

In the various embodiments, the vision-testing methods described below are intended to test the near vision of the individual 10.

A first embodiment of a method for testing the vision of an individual 10 and that may be implemented by an optician to evaluate the near-vision vision quality of said individual 10 and possibly to prescribe a suitable visual correction to this individual 10 will now be described with reference to FIGS. 1 and 2.

According to a first step of the vision-testing method, the optician gives the individual 10 the tablet 20 on the screen 21 of which the test image 22 is displayed.

In a second step, the optician places the individual 10, or indeed asks the individual 10 to place himself, so as to observe the screen 21 with a natural cephalic carriage, i.e. so that his head is in the position that he finds most natural for observation of the screen 21.

In other words, in the second step, the optician asks the individual 10 to look at the test image 22 displayed on the screen 21 while holding the tablet 20 at the observation distance D1, which here corresponds to a near-vision observation distance that is for example equal to 40 centimeters.

One of the objectives of this step is to place the individual 10 in a situation similar to that which he encounters in his everyday life when looking at images or reading text in near vision.

In a third step of the invention and in the configuration resulting from the first and second steps described above, a first border 23 on the screen 21 of the tablet 20 (see FIG. 2) is determined.

This first border 23, which is here determined for a given position of the head 11 of the individual 10 with respect to the screen 21 of the tablet 20, is defined as being a border of zones of optimal/degraded vision of the test image 22 by the individual 10, in the sense that it bounds in the visual field of the individual 10, on the one hand, a zone of optimal vision 23A, and, on the other hand, a zone of degraded vision 23B (see FIG. 2).

More precisely, the first border 23 of the zones of optimal/degraded vision may be determined by virtue of guidance given by the optician who asks the tested individual 10 to indicate:

the one or more zones of the test image 22 of the visual test that he is able to see optimally: this is here the case for the zone of optimal vision 23A, and the one or more zones of the test image 22 of the visual test that he sees only degradedly: this is here the case for the zone of degraded vision 23B.

Here, for the test image 22 and for the near-vision observation distance D1, the individual 10 declares:

that he is able to see the zone of optimal vision 23A optimally, and that he is only able to see the zone of degraded vision 23B hazily.

The vision-testing method described above especially allows the hypermetropia of young or the presbyopia of old subjects with particularly degraded near vision to be tested.

In other embodiments of the invention, the individual determines the border of zones of optimal/degraded vision depending on another performance criterion that may for example be the contrast of the test image, the distortion of the images or patterns in the test image, colors, or any other criterion that the individual judges to be relevant.

In order to allow the first border 23 to be embodied, the vision-testing device includes means for inputting this first border 23.

In the embodiments shown in FIGS. 1 and 3, in which embodiments the vision-testing device includes a touch tablet 20, the inputting means especially comprise the screen 21 of the tablet 20, on which the individual 10 may draw, for example by means of one of his free fingers, the first border 23 on the screen 21.

By "draw", what is meant here is that the individual defines the location of the first border with respect to the screen of the tablet.

Thus, as a variant, the individual could draw the first border on the screen by means of a pointing device such as a computer mouse or a plotter equipped with a digital pen.

As another variant, the individual could indicate orally through which points the path of the first border passes. This oral indication may be given at the opticians or indeed remotely, directly or indirectly.

The tablet 20 is here designed and programmed to follow the path drawn by the individual 10 on the screen 21. The path followed by the free finger of the individual 10 on the screen 10 of the tablet 20 thus forms the first border 23 of zones of optimal/degraded vision depending on the criterion chosen by the individual 10.

Advantageously, the tablet 20 may also display the first border 23 as, and at the same time as, the free finger of the individual 10 is moved over the screen 21.

In other words, the vision-testing device here formed by the tablet 20 includes drawing means, here the screen 21, for superposing the test image 22 and the first border 23 determined by the individual 10 in the third step of the vision-testing method.

At the end of the third step, for a predetermined near-vision observation distance D1, a first border 23 has been determined and displayed on the screen 21 of the tablet 20, in superposition on the test image 22, this first border 23 separating a zone of optimal vision 23A of the screen 21, which the individual 10 is able to see clearly, and a zone of degraded vision 23B, which the individual 10 sees only hazily.

From the first border 23 determined in the third step, it is possible to deduce a first border indicator relating to this first border 23.

This first border indicator is a datum representative of the vision quality of the individual 10 as measured by the vision-testing method.

In the example in FIG. 2, this first border indicator may correspond to the position of this first border 23 with respect to the test image 22 displayed on the screen or even to the shape of this first border 23.

This first border indicator may also correspond to the area (expressed in square centimeters for example) of the zone of optimal vision 23A, i.e. the area under the first border 23, or to that of the zone of degraded vision 23B (surface above the first border 23), or even to the ratio of one of these two areas to the total area of the test image 22 or the total area of the screen 21.

Thus, in one preferred embodiment, the vision-testing method includes a fourth step consisting in recording the first border indicator.

To this end, the vision-testing device includes means for storing in memory this indicator.

More precisely here, the tablet 20 is equipped with a digital storage medium (not shown) in which the position and/or the shape of the first border 23 on the screen 21 are stored.

In another preferred embodiment, the vision-testing method includes a fifth step that consists, in a first part, in comparing with a reference indicator the border indicator deduced from the preceding fourth step from the border of zones of optimal/degraded vision, said border being determined on the screen of the tablet by the individual.

In order to allow this comparison, this reference indicator is chosen in correspondence with the first border indicator. What is meant by that is that the first border indicator determined in the fourth step of the vision-testing method relates to the position and/or area of the corresponding first border 23, whereas the reference indicator relates to a reference position and to a reference area. This situation is that in FIGS. 1 and 2.

Thus, the reference position and/or area may for example correspond to an average position and/or area measured with a plurality of individuals, or indeed measured with the individual 10 in FIG. 1 during many preceding tests.

In a second part of the fifth step, it is therefore possible to deduce from the preceding comparison of the first border indicator and the reference indicator an optical performance of the individual 10 under the observation conditions resulting from the first and second steps.

In other words, the comparison of the first border indicator with the reference indicator allows the variation in the position and/or area of the first border 23 of zones of optimal/degraded vision to be evaluated. For the individual 10 in FIG. 1, in the case where, as seen above, the reference indicator comprises an average position and/or area, it is thus possible to reveal whether the near vision of the individual 10 has degraded or not over time, if for example the area of the zone of optimal vision 23A has decreased. The optical performance tested and deduced from the comparison of the first border indicator and the reference indicator therefore here corresponds to the visual field accessible in near vision by the individual 10.

According to one variant of the vision-testing method described above, it is possible, in a step subsequent to the fourth step, to determine from the first border indicator recorded on the digital storage medium of the tablet 20, a recommended optical design of a piece of vision-correcting ophthalmic equipment recommended for the individual 10.

According to this variant, the optical powers of the ophthalmic lenses of the piece of ophthalmic equipment recommended for the individual 10 are determined from the position and/or area of the first border 23 on the screen 21 of the tablet 20.

At the end of this step, the optician is able to advocate to the individual 10 a particular ophthalmic-equipment optical design that will be able to correct his vision, here his near vision.

According to a second embodiment of the vision-testing method according to the invention, which will be described with reference to FIGS. 1 to 6, the first, second and third steps of the method are executed such as described above with the individual 10, who here is not equipped with a first piece of vision-correcting equipment, to determine the first border 23 (third step) and record the first border indicator (fourth step) in a digital memory of the tablet 20.

According to this second embodiment, the individual 10 is here actually equipped with a second piece of vision-correcting ophthalmic equipment 14 (see FIG. 3). This second piece of ophthalmic equipment 14 is typically a spectacle frame comprising two progressive ophthalmic lenses for correcting near and far vision.

Here, the optical design of this second piece of ophthalmic equipment 14 is considered to have been determined by the optician by virtue of the first border 23 of zones of optimal/degraded vision and by virtue of the first border indicator.

This second embodiment of the vision-testing method may then advantageously be implemented to check this second piece of ophthalmic equipment 14, for example when it is given to the individual 10 whose vision quality was tested beforehand.

As shown in FIG. 3, when the individual 10 observes, with a natural cephalic carriage, the test image 22 displayed on the screen 21 of the tablet 20, this test image is here located at the predetermined observation distance D2 for near vision. This predetermined observation distance D2 is here equal to 35 cm.

The individual 10 determines, on the screen 21 of the tablet 20, a second border 24 of zones of optimal/degraded vision of the test image 22 by the individual 10 (see FIG. 6), in the same configuration as the first and second steps implemented to determine the first border 23.

Figure 6:
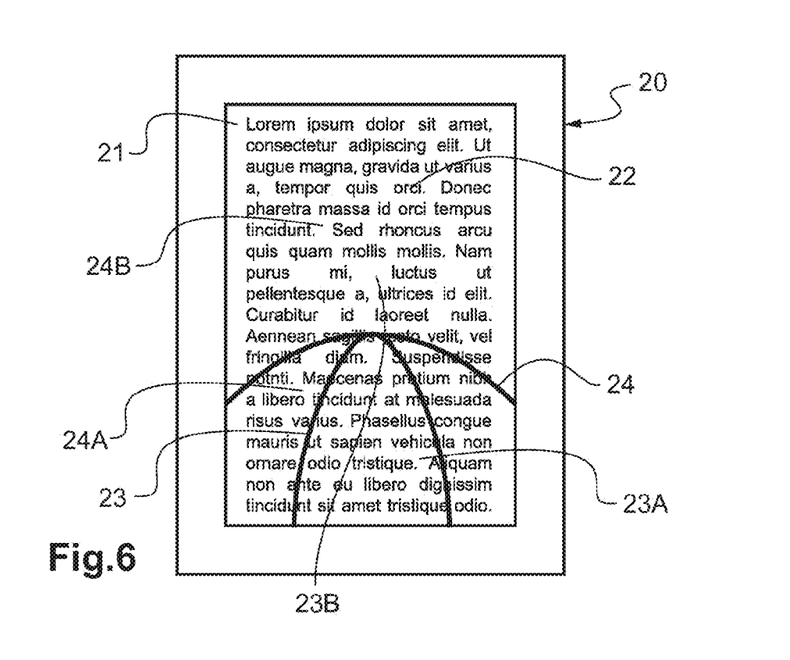
FIG. 6 is a schematic view of the text displayed on the touch tablet in FIGS. 1 and 3 and on which are displayed in superposition two sound borders determined by the individual under the conditions of FIGS. 1 and 3, respectively.

In the same way as above, the second border 24 respectively bounds a second zone of optimal vision 24A and a second zone of degraded vision 24B of the visual field of the individual 10, for which zones the individual 10, equipped with the second piece of ophthalmic equipment 14, indicates whether he respectively sees optimally or degradedly the test image 22 of the visual test, which image is displayed on the screen 21 of the tablet 20.

Figure 4:
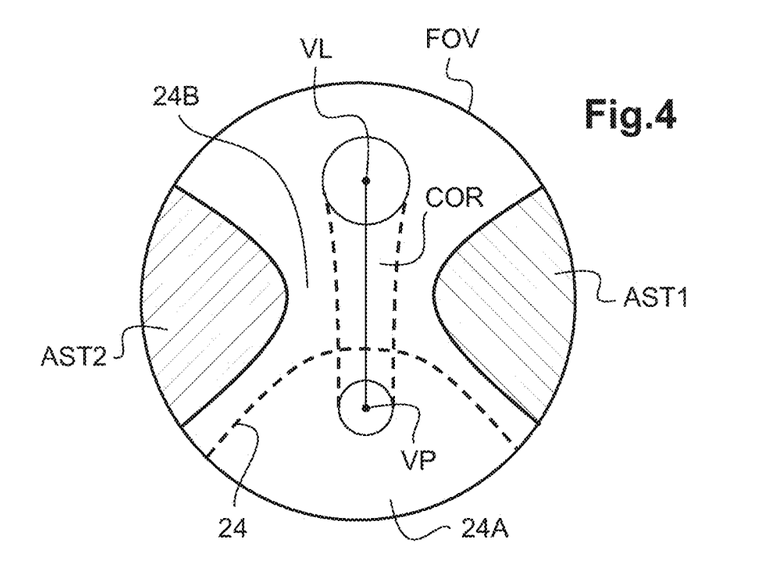
FIG. 4 is a schematic representation of the visual field of the individual in FIG. 3 through his piece of ophthalmic equipment.

FIG. 4 shows a schematic view of the visual field FOV of the individual 10 through his second piece of ophthalmic equipment 14 comprising progressive lenses.

In FIG. 4 are also shown:

the near-vision point VP, which is generally located in the bottom portion of the visual field of the individual 10 wearer of the second piece of ophthalmic equipment 14, the far-vision point VL, which is for its part located in the top portion of the visual field, the point VL and the point VP defining a corridor COR of visual correction along which corridor the optical power of the progressive lenses varies (in the sense that their powers increase as the distance to the point VP decreases), and zones of astigmatism AST1, AST2, which are characteristic of a progressive lens and in which the vision of the individual 10 is degraded because of the astigmatism of the progressive lenses, at the edge of the visual field FOV.

FIG. 4 also shows the second border 24 of zones of optimal/degraded vision, this second border 24 therefore here relating to the near vision of the individual (see the configuration in FIG. 3) and therefore being close to near-vision point VP that moreover forms part of the second zone of optimal vision 24A whereas the zones of astigmatism AST1, AST2 (zones of visual discomfort) form, for their part, the zone of degraded vision 24B that the individual 10 indicates as seeing degradedly through the second piece of ophthalmic equipment 14.

Figure 5:
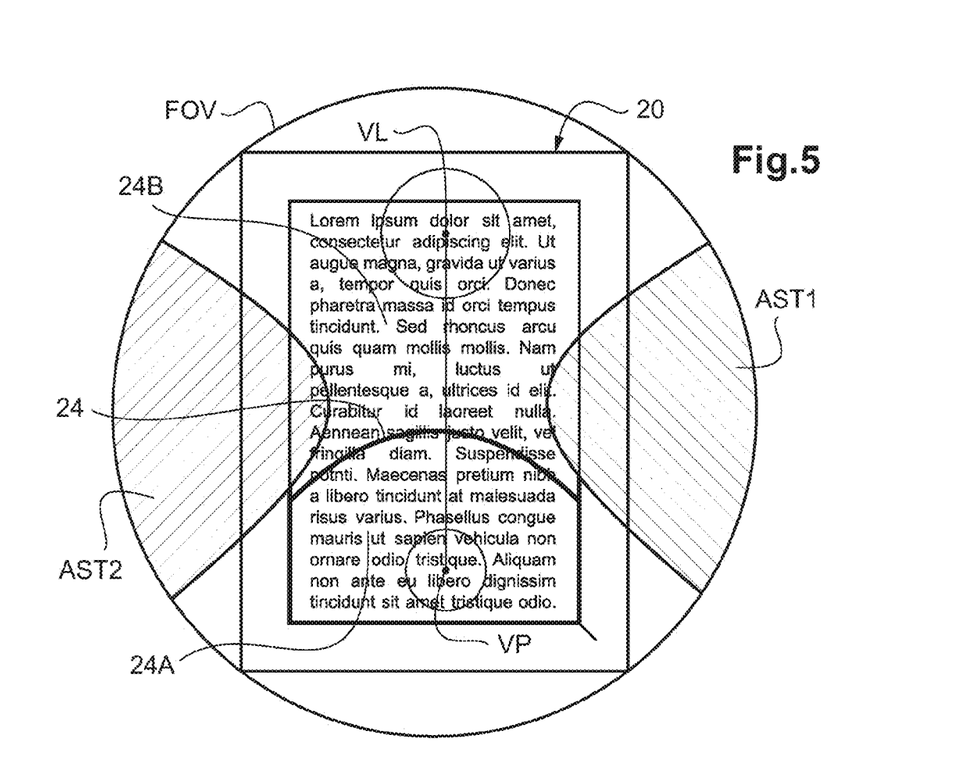
FIG. 5 is a schematic view in which the text displayed by the tablet under the conditions of FIG. 3 and the visual field of FIG. 4 are superposed.

FIG. 5 shows in superposition, on the one hand, the test image 22 displayed on the screen 21 of the tablet 20 and, on the other hand, the visual field FOV of the individual 10, thus showing which portions of the test image 22 are seen optimally and degradedly in the visual field FOV of the individual 10.

According to the second embodiment, and as FIG. 6 clearly shows, the test image 22, the first border 23 and the second border 24 are displayed in superposition on the screen 21 of the tablet 20.

Moreover, in the same way as for the first border 23, a second border indicator that is representative of the second border 24 of the zones of optimal/degraded vision is then determined and recorded.

This second border indicator comprises the position and shape of the second border 24 with respect to the test image 22 displayed on the screen 21 of the tablet 20 (see for example FIG. 5).

Next, the first border indicator and the second border indicator are compared.

For example, on the one hand the positions of the first and second borders 23, 24 are compared with each other, and, on the other hand, the respective areas of the first and second zones of optimal 23A, 24A or degraded 23B, 24B vision are compared with each other.

As is shown in FIG. 6, it is for example noted that the individual 10 indicates that he is able to see clearly, with the second piece of ophthalmic equipment 14, in a second zone of optimal vision 24A that is larger than the first zone of optimal vision 23A i.e. the zone determined without ophthalmic equipment.

Thus, by superposing the test image 22, the first border 23 and the second border 24, the individual 10 may appreciate the gain in visual field for which he sees optimally.

Therefore, from the comparison of the first border indicator and the second border indicator, an optical performance of the individual 10 under the observation conditions of the first and second steps, when the individual 10 observes the test image 22 displayed on the screen 21 of the tablet 20 at the predetermined observation distance D2, is deduced.

In a third embodiment in which, initially, the individual is actually equipped with an initial piece of vision-correcting ophthalmic equipment, for example progressive lenses such as those of the second piece of ophthalmic equipment 12 in FIG. 3, it is possible to determine an initial border of zones of optimal/degraded vision and to record an initial border indicator thereof by virtue of the individual observing, at the predetermined initial observation distance, the test image displayed on the screen of the tablet.

Next, the individual being actually or virtually equipped with another piece of vision-correcting ophthalmic equipment different from this initial piece of ophthalmic equipment, another border of zones of optimal/degraded vision of the visual field of the individual is determined on the screen of the tablet.

When the individual is virtually equipped with the other piece of ophthalmic equipment, this other border is then determined by numerical simulation of the visual field of the individual observing the test image under the same conditions as those of the first and second steps, i.e. at the initial observation distance and with a natural cephalic carriage.

The numerical simulation of the visual field of the individual is carried out on the basis of knowledge:
of the position and orientation of the head of the individual with respect to the screen of the tablet, when the individual adopts a natural cephalic carriage,
of the predetermined initial observation distance,
of the visual correction of the initial piece of ophthalmic equipment, and
of the test image displayed on the screen of the tablet.

Preferably, the other piece of vision-correcting ophthalmic equipment to obtain after numerical simulation is a piece of ophthalmic equipment that improves the border indicator deduced from the determination of the other border of zones of optimal/degraded vision. For example, this other piece of ophthalmic equipment will possibly advantageously enlarge the zone of optimal vision or shrink the zone of degraded vision that the individual sees through this other piece of ophthalmic equipment.

This third embodiment may advantageously be implemented by an optician desiring to advise the individual as to a new piece of ophthalmic equipment, when the vision quality of an individual already actually wearing a piece of vision-correcting ophthalmic equipment has changed.

In other embodiments, the vision-testing device may comprise means for pinpointing the posture of the head of the individual with respect to the screen of the tablet.

Such pinpointing means may for example comprise a pinpointing clip fastened to the piece of ophthalmic equipment worn by the individual, such as that described in document EP 2137569.

In this case, it is then advantageous to determine the border of zones of optimal/degraded vision with a test image of the visual test the position of which on the screen of the tablet depends on the position of the head of the individual with respect to the screen of the tablet.

In another embodiment, advantage may be taken of the zone of optimal vision, in which the individual sees optimally for the predetermined observation distance with his natural cephalic carriage, in order to carry out complimentary visual tests.

Thus, in this other embodiment, the vision-testing method comprises a sixth step in which, on a useful area of the screen of the tablet corresponding to a useful zone comprised in the zone of optimal vision of the visual field of the individual, a complementary visual test comprising a complimentary test image, which will therefore be seen optimally by the individual, is displayed.

This then allows the complementary visual tests to be carried out under better conditions.

This also allows the border of zones of optimal/degraded vision and a result obtained from this complementary visual test to be displayed in superposition.

In vision-testing methods in which the intermediate or far vision of the individual 10 is tested, a device such as a remotely controlled handset or wireless pointer may be used to trace the border (23) of zones of optimal/degraded vision of said test image (22).

The invention claimed is:

1. A method for testing the vision of an individual (10) wearing a piece of vision-correcting ophthalmic equipment, said method including the following steps:
   a) placing said individual (10) at a predetermined observation distance (D1) from a displaying area (21), at which said individual (10) observes, with a natural cephalic carriage, said displaying area (21), and
   b) displaying, on said displaying area (21), a visual test comprising at least one test image (22), and
   c) determining, in said displaying area (21), a border (23) of zones of optimal/degraded vision of said test image (22) by the individual (10) in the configuration resulting from steps a) and b), said border (23) respectively bounding, in a visual field of said individual (10) equipped with said piece of ophthalmic equipment, a zone of optimal vision (23A) and a zone of degraded vision (23B) of said visual field, for which zones said individual (10) indicates whether he respectively sees optimally or degradedly said test image (22) of the visual test through said piece of vision-correcting ophthalmic equipment, and
   d) recording a border indicator representative of said border (23) of zones of optimal/degraded vision,
   wherein:
   steps a) to d) are executed at least a first time, with an individual (10) equipped with a first piece of vision-correcting ophthalmic equipment, to determine a first border (23) and to record a first border indicator,
   the individual (10), actually or virtually being equipped with a second piece of vision correcting ophthalmic equipment (14) that is different from said first piece of ophthalmic equipment, a second border (24) of zones of optimal/degraded vision of said test image (22) by said individual (10) is determined in said displaying area (21) in the configuration resulting from steps a) and b), said second border (24) respectively bounding a second zone of optimal vision (24A) and a second zone of degraded vision (24B) of said visual field (FOV), for which zones said individual (10) actually or virtually equipped with said second piece of ophthalmic equipment (14) indicates or is assumed to respectively see optimally or degradedly said test image (22) of the visual test, a second border indicator representative of said second border (24) of zones of optimal/degraded vision is recorded, said first border indicator and said second border indicator are compared, and from the preceding comparison an optical performance of the individual (10) under the observation conditions of steps a) and b) is deduced.

2. The vision-testing method as claimed in claim 1, wherein, in step d), the border indicator corresponds to the position and/or shape of said border (23).

3. The vision-testing method as claimed in claim 2, wherein said second border (24) is determined by executing a second time steps a) to c) for said individual (10) equipped with a real example of said second piece of ophthalmic equipment (14).

4. The vision-testing method as claimed in claim 2, wherein said second border (23) is determined by numerical simulation of the visual field (FOV) of said individual (10) virtually equipped with said second piece of ophthalmic equipment (14) and observing the test image (22) under the same conditions as those of steps a) and b).

5. The vision-testing method as claimed in claim 2, wherein, in step c), said border (23, 24) of zones of optimal/degraded vision is determined by the individual (10) who draws said border (23, 24) in said displaying area (21).

6. The vision-testing method as claimed in claim 1, wherein said second border (24) is determined by executing a second time steps a) to c) for said individual (10) equipped with a real example of said second piece of ophthalmic equipment (14).

7. The vision-testing method as claimed in claim 1, wherein said second border (23) is determined by numerical simulation of the visual field (FOV) of said individual (10) virtually equipped with said second piece of ophthalmic equipment (14) and observing the test image (22) under the same conditions as those of steps a) and b).

8. The vision-testing method as claimed in claim 1, including a step f) in which, on a useful area of the displaying area (21) corresponding to the zone of optimal vision (23A) of the visual field of the individual (10) equipped with said piece of vision-correcting ophthalmic equipment, a complementary visual test comprising at least one complementary test image is displayed.

9. The vision-testing method as claimed in claim 1, wherein the test image (22), the first border (23) and the second border (24) are displayed in superposition.

10. The vision-testing method as claimed in claim 1, wherein, in step c), said border (23, 24) is determined for a given position of the head (11) of the individual (10) with respect to the displaying area (21).

11. The vision-testing method as claimed in claim 1, wherein, in step b), the position of the test image (22) of said visual test in said displaying area (21) depends on the position of the head (11) of the individual (10) with respect to the displaying area (21).

12. The vision-testing method as claimed in claim 1, wherein, in step c), said border (23, 24) of zones of optimal/degraded vision is determined by the individual (10) who draws said border (23, 24) in said displaying area (21).

13. A device for testing the vision of an individual (10) wearing a piece of vision-correcting ophthalmic equipment, said device including:

displaying means (20) suitable for displaying on a displaying area (21), a visual test comprising at least one test image (22);

means for inputting (20), in said displaying area (21), a border (23, 24) of zones of optimal/degraded vision of said test image (22) by the individual (10), said border (23, 24) respectively bounding, in a visual field (FOV) of said individual (10), a zone of optimal vision (23A, 24A) and a zone of degraded vision (23B, 24B) of said visual field (FOV), for which zones said individual (10) indicates whether he respectively sees optimally or degradedly said test image (22) of the visual test through said piece of vision-correcting ophthalmic equipment;

means for storing in memory the position and shape of said border (23, 24) in the displaying area (21); and means for pinpointing the posture of the head (11) of said individual (10) with respect to the display means (20).

14. The vision-testing device as claimed in claim 13, including drawing means (21) suitable for superposing said test image (22) and at least said border (23, 24).

\* \* \* \* \*